United States Patent [19]

Eayre et al.

[11] Patent Number: 5,668,008

[45] Date of Patent: Sep. 16, 1997

[54] AVIRULENT GEOTRICHUM CANDIDUM FOR BIOLOGICAL CONTROL OF POSTHARVEST ROTS ON FRUIT

[75] Inventors: Cynthia G. Eayre, Weslaco; Mani Skaria, McAllen, both of Tex.

[73] Assignees: The United States of America, as represented by the Secretary of Agriculture, Washington, D.C.; The Texas A&M University System, College Station, Tex.

[21] Appl. No.: 508,358

[22] Filed: Jul. 28, 1995

[51] Int. Cl.$^6$ ..................................................... C12N 1/14
[52] U.S. Cl. ...................... 435/254.1; 426/49; 426/102; 426/532; 426/615
[58] Field of Search ................................... 435/254.1

[56] References Cited

U.S. PATENT DOCUMENTS

| | | | |
|---|---|---|---|
| 4,975,277 | 12/1990 | Janisiewicz et al. | 435/253.3 |
| 5,041,384 | 8/1991 | Wilson et al. | 435/255 |
| 5,413,783 | 5/1995 | McLaughlin et al. | 435/938 |
| 5,470,741 | 11/1995 | Oester et al. | 435/254.1 |

*Primary Examiner*—Herbert J. Lilling
*Attorney, Agent, or Firm*—M. Howard Silverstein; Randall E. Deck; John D. Fado

[57] ABSTRACT

A novel avirulent strain of *Geotrichum candidum* has been isolated which is effective to inhibit growth of postharvest pathogens on fruit. In use, protection from postharvest fruit-rots may be afforded by application of an effective amount of the strain onto the surface of fruit.

6 Claims, No Drawings

AVIRULENT GEOTRICHUM CANDIDUM FOR BIOLOGICAL CONTROL OF POSTHARVEST ROTS ON FRUIT

BACKGROUND OF THE INVENTION

1. Field of the Invention

The invention relates to a strain of *Geotrichum candidum* for use in the biological control of postharvest rots on fruit, particularly citrus.

2. Description of Related Art

Damage to fruit caused by fungal post-harvest diseases results in significant economic losses to the fruit and citrus industry worldwide. Included among some of the more destructive post-harvest pathogens or molds affecting citrus are *Penicillium digitatum*, *Geotrichum candidum* (Link ex Pers), and *Penicillium italicum*. Conventional techniques for control of these pathogens have relied upon the application of fungicides after harvest or prior to shipping. However, the extensive use of fungicides has been the subject of increasing public concern as posing potential hazards to human health and the environment. Moreover, fungicides are often ineffective with the development of fungicide-resistant strains of the pathogens.

To illustrate the scope of the problem, green mold of citrus, caused by *P. digitatum*, is the major postharvest disease of citrus in south Texas, and is one of the two diseases responsible for the majority of decay losses in the California and Arizona citrus industries (the other being blue mold, caused by *P. italicum*). TBZ and imazalil are the fungicides currently used for control of green mold in these regions. However, due to very low residue tolerances for TBZ in Europe, TBZ may not be used on fruit used for juice destined for that market. Moreover, the effectiveness of TBZ against green mold is not optimal. Therefore, green mold on citrus remains a serious problem, even on citrus treated with TBZ.

Recently, techniques involving the postharvest treatment of fruits with antagonistic microorganisms have been developed which have shown promise for the control of postharvest pathogens. For example, Pusey et al. (1986, Plant Dis., 86:753–756) controlled brown rot in peaches, caused by *Monilinia fructicola*, with the bacterium *Bacillus subtilis*. Roberts (U.S. Pat. No. 5,244,680) disclosed strains of *Cryptococcus* effective for the control of postharvest rots, as well as a method for selecting bacteria and yeasts effective as biocontrol agents. Wilson et al. (U.S. Pat. No. 5,425,941) also isolated strains of *Candida oleophila* effective for controlling a number of different postharvest diseases on fruit.

SUMMARY OF THE INVENTION

We have now discovered an avirulent strain of *Geotrichum candidum* which is effective to inhibit growth of postharvest pathogens on fruit. Protection of a variety of fruits from postharvest rots may be accomplished by application of an effective amount of the strain onto the surface of the fruit.

In accordance with this discovery, it is an object of this invention to provide a novel microorganism for use as a biocontrol agent to control postharvest diseases in fruit.

Another object of this invention is to provide a biocontrol agent which is both safe and effective for the control of postharvest diseases in fruit, without the use of chemical fungicides.

Other objects and advantages of this invention will become readily apparent from the ensuing description.

DETAILED DESCRIPTION OF THE INVENTION

The preferred fungus for use in this invention is a novel strain of *Geotrichum candidum* Link ex Pers (teleomorph *Endomyces geotrichum* Butler & Peterson). The parent strain was originally isolated in pure form from rotten citrus fruit in south Texas, and was classified as *G. candidum* Link ex Pers, based upon its characteristic morphology and colonial appearance. After frequent subculturing on solid culture media over an extended period of time, we unexpectedly discovered that the strain became both avirulent and capable of reducing the incidence of postharvest disease when applied to wounded fruit. This avirulent strain effective for controlling postharvest diseases was recovered and designated *Geotrichum candidum* strain AVIR.

The above-mentioned *Geotrichum candidum* strain AVIR has been deposited under the Budapest Treaty in the Agricultural Research Service Culture Collection (NRRL) in Peoria, Ill., on Jul. 27, 1995 and has been assigned Deposit no. NRRL 21488.

Morphologically, *G. candidum* strain AVIR has hyaline and septate mycelia, which are specialized into broad, radiating, vegetative hyphae which branch dichotomously, and narrower, lateral, sporulating hyphae, which may also branch. Arthrospores are readily formed by segmentation or breakage of the hyphae. The strain grows rapidly on potato-dextrose agar (PDA) at room temperature, producing dull white colonies, having a dry, wrinkled appearance with no aerial mycelia.

For the purpose of this invention, any isolate of *Geotrichum candidum* having the identifying characteristics of strain AVIR, including subcultures and variants thereof which are avirulent and retain the ability to inhibit growth of postharvest pathogens on fruit, are effective. The term variants is defined herein to include transformants and mutants of *G. candidum* strain AVIR which are avirulent and are capable of inhibiting growth of postharvest pathogens on fruit.

The fungi of this invention may be cultivated by conventional techniques under any convenient aerobic conditions that are effective to promote growth. In accordance with the preferred embodiment, the fungi are inoculated and grown on conventional solid-phase mycology culture media. Although several culture media may be employed, including Nutrient agar or tryptic soy agar, potato-dextrose agar is preferred. The fungi will grow over wide temperature and pH ranges, generally between about 10° to 33° C. and about 6.5 to 7.5, respectively, with room temperature and a pH of about neutral being preferred. Once a sufficiently heavy growth of the fungus has obtained, usually in about 4 to 5 days, spores may be recovered, for example, by scraping the colonies with a bladed instrument such as a spatula or scalpel. When harvested in this manner, the arthrospores readily break from the hyphae, adhering to the scraping instrument. Harvested spores may be stored in a dry environment, frozen or lyophilized, or they may be dispersed in a suitable carrier such as water or buffer, until used.

Alternatively, the fungi may be grown by culture in liquid media, particularly with agitation. Preferred liquid media include Nutrient broth, tryptic soy broth, and particularly potato-dextrose broth. When grown in large scale vessels, the culture media should also be aerated for optimal growth. The mycelia readily disintegrate into arthrospores when shaken in aqueous media, allowing the spores to be easily harvested after incubation. Fungal spores and remaining mycelial fragments may be recovered from the media using conventional techniques, such as by filtration or centrifugation, and stored as described hereinabove.

Commercial formulations containing the fungi may be prepared from spores and/or mycelia which have been harvested from the culture medium such as described hereinabove. In the preferred embodiment, spores of the fungus are harvested and formulated as a suspension or emulsion in a suitable agronomically acceptable inert carrier or vehicle. Preferred carriers include but are not limited to water, buffers, or vegetable or plant oils. The spores may also be formulated with solid inert carriers such as talc, clay or vermiculite, or incorporated into conventional controlled release microparticles or microcapsules. Further still, the fungi may be incorporated into waxes or protective coatings such as described by Nisperos-Carriedo and Baldwin (U.S. Pat. No. 5,198,254). The skilled practitioner will recognize that the fungi may be formulated in combination with conventional additives such as emulsifying agents, surfactants or wetting agents, antioxidants, insecticides, or even with fungicides which exhibit low toxicity to the subject fungi.

The absolute amount of the fungi and their concentration in the final composition are selected to provide an effective inhibition of growth of postharvest pathogens on fruit. An effective amount is defined herein as that quantity of spores and mycelia that result in a significant inhibition or prevention of growth of a targeted fruit pathogen when applied to the fruit relative to an untreated control. Suitable amounts and concentrations may be readily determined by routine testing, and may vary considerably depending upon the target pathogen, the type of fruit being treated and its ripeness and condition (i.e., wounding), mode of application, formulation, environmental conditions such as temperature and humidity, and other related factors. Without being limited thereto, it is envisioned that a concentration of about $10^3$ to $10^6$ spores or CFU of the fungi of this invention per ml will be effective.

In use, the fungi may be applied directly upon fruit using conventional techniques. Fruit may be treated either before or after harvest. However, compositions of the fungi will typically be applied upon harvested fruit by spraying, dipping or brushing, although solid formulations may be applied by dusting as well. For optimal inhibition of postharvest rots, the fungi should be applied to the fruits immediately after harvest or as early as possible thereafter, preferably prior to shipment or storage.

The fungi of this invention are effective in controlling postharvest pathogens on a variety of fruits. Without being limited thereto, pathogens of particular interest which may be inhibited by treatment of fruit with these fungi are agronomically important pathogens, especially *Penicillium digitatum*, wild type *Geotrichum candidum* (Link ex Pers), *Penicillium italicum*, and *P. ulaiense*, the causative agents of green mold, sour rot, blue mold, and whisker mold, respectively, on citrus. Moreover, while the fungi are particularly effective for controlling postharvest rots on citrus, including grapefruit, oranges, lemons and limes, it is also envisioned that the fungi will be effective for controlling postharvest rots on other fruits, including but not limited to peaches, nectarines, apples, pears and strawberries.

The following examples are intended only to further illustrate the invention and are not intended to limit the scope of the invention which is defined by the claims.

EXAMPLE 1

Efficacy of *G. candidum* strain AVIR was examined using varieties of grapefruits (Rio Red), navel oranges, and oranges (Marrs) grown at the Texas A&M-Kingsville Citrus Center in Weslaco, Tex.

Using an Anderson air sampler, the laboratory room in which the experiments were to be conducted was found to be contaminated with spores of naturally occurring *Penicillium digitatum*. Fruit were harvested but were not washed, leaving any naturally occurring *P. digitatum* inocula and allowing inoculation via room air. Therefore, no *P. digitatum* challenge inoculum was added to the fruit. The day of harvest, fruit were randomly divided into ten groups of 10 fruit each, and punctured twice with a nail (6 mm deep). The wounds of each fruit in the test groups were inoculated with 10 μl of a spore suspension of *G. candidum* strain AVIR ($10^3$ spores/μl), while the wounds of control fruit were inoculated with 10 μl sterile water. Fruit were stored in plastic bags at 22° C. Incidence of postharvest disease green mold caused by *P. digitatum* was recorded after 7 days. Each test included 5 replications of 10 fruit each, and tests were run three times with grapefruit and three times with oranges. Results were analyzed by a one tailed t test.

The results are shown in Table 1. Fruit treated with *G. candidum* strain AVIR exhibited a significantly lower incidence of green mold than controls. Decay rates on some treated fruit were substantial because the tests were conducted with wounded fruit. Decay rates with intact fruit treated with *G. candidum* strain AVIR are much lower.

It is understood that the foregoing detailed description is given merely by way of illustration and that modifications and variations may be made therein without departing from the spirit and scope of the invention.

TABLE 1

| | Percent of fruit rotted | | |
|---|---|---|---|
| Trial | Control | Treatment | |
| 1 | 45 | 10 | navels |
| 2 | 12 | 0 | grapefruit |
| 3 | 18 | 5 | grapefruit |
| 4 | 94 | 76 | marrs orange |
| 5 | 98 | 84 | marrs orange |

We claim:

1. A strain of *Geotrichum candidum* having all the identifying characteristics of *Geotrichum candidum* strain NRRL 21488, which is avirulent and effective to inhibit growth of postharvest pathogens on fruit.

2. A strain of *Geotrichum candidum* as described in claim 1 which is substantially biologically pure.

3. A composition for controlling postharvest diseases in fruit comprising said strain of *Geotrichum candidum* of claim 1 and an agronomically acceptable inert carrier.

4. A composition as described in claim 3 wherein said carrier comprises water.

5. A composition as described in claim 4 wherein said strain of *Geotrichum candidum* is present in an amount effective to inhibit growth of postharvest pathogens on fruit.

6. A composition as described in claim 4 wherein said strain of *Geotrichum candidum* is encapsulated.

* * * * *